United States Patent
Ravetta et al.

[11] Patent Number: 5,981,795
[45] Date of Patent: Nov. 9, 1999

[54] METHOD FOR THE N-DENITRATION OF N-NITRO-DINITROANILINE IN A HOMOGENEOUS PHASE

[75] Inventors: Guido Ravetta, Milan; Gianluca Bernardi, Brescia, both of Italy

[73] Assignee: Finchimica S.p.A., Manerbio, Italy

[21] Appl. No.: 09/288,381

[22] Filed: Apr. 8, 1999

[51] Int. Cl.⁶ .................................................. C07C 209/00
[52] U.S. Cl. .......................................... 562/437; 564/411
[58] Field of Search .............................................. 564/437

[56] References Cited

U.S. PATENT DOCUMENTS 4,226,789  10/1980  Eizember et al. .
5,663,441   9/1997  Kwiatkowskis et al. .
5,689,006  11/1997  Kwiatkowskis et al. .

FOREIGN PATENT DOCUMENTS 0870755  10/1998  European Pat. Off. .

*Primary Examiner*—Paul J. Killos
*Attorney, Agent, or Firm*—Donald L. Rhoads; Kramer Levin Naftalis & Frankel LLP

[57] ABSTRACT

A method of purifying dinitroaniline of the general formula:

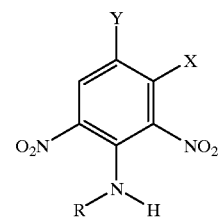

in which:

R is linear or branched $C_1$–$C_6$ alkyl, $C_4$–$C_6$ cycloalkyl, $C_1$–$C_4$ monohaloalkyl or $C_1$–$C_4$ alkoxy($C_2$–$C_4$)alkyl, Y is $C_1$–$C_4$ alkyl, halogen or $CF_3$, and X is hydrogen, halogen, $C_1$–$C_4$ alkyl, $C_1$–$C_4$ alkoxy, $C_1$–$C_4$ monohaloalkyl, or $C_1$–$C_4$ alkoxy($C_1$–$C_4$)alkyl, by N-denitration of the impurities of N-2,6-dinitroaniline contained therein, in the presence of a base selected from alkali-metal hydroxides, alkali-metal carbonates and ammonium hydroxide, at neutral or basic pH, comprising the treatment, with stirring, of the dinitroaniline to be purified, with an alcoholic organic solvent.

8 Claims, No Drawings

METHOD FOR THE N-DENITRATION OF N-NITRO-DINITROANILINE IN A HOMOGENEOUS PHASE

DESCRIPTION

The present invention relates to a method of purifying dinitroaniline having herbicidal activity by N-denitration of the N-nitro-dinitroaniline impurities contained therein.

Dinitroanilines having herbicidal activity, the purification of which is the object of the method of the present invention, are compounds of the general formula:

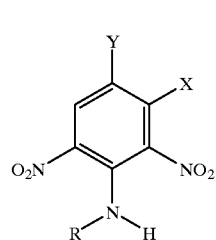

(I)

in which:
R is linear or preferably branched $C_1$–$C_6$ alkyl, $C_4$–$C_6$ cycloalkyl, $C_1$–$C_4$ monohaloalkyl or $C_1$–$C_4$ alkoxy($C_2$–$C_4$)alkyl,
Y is $C_1$–$C_4$ alkyl, halogen or $CF_3$, and
X is hydrogen, halogen, $C_1$–$C_4$ alkyl, $C_1$–$C_4$ alkoxy, $C_1$–$C_4$ monohaloalkyl, or $C_1$–$C_4$ alkoxy($C_1$–$C_4$)alkyl.

Of particular interest are compounds in which $R_1$ is hydrogen, $R_2$ is 1-ethylpropyl, Y is methyl or isopropyl, and X is methyl or methoxymethyl and, in particular, the compound N-(1-ethylpropyl)-2,6-dinitro-3,4-dimethylaminobenzene, known commercially as Pendimetalin.

The aforementioned compounds can be produced by the nitration or dinitration of corresponding substituted anilines.

It is known that, in the course of the aniline nitration or dinitration process, variable quantities of undesired impurities of various kinds are formed, amongst which are N-nitro-dinitroanilines (N,2,6-trinitroanilines) of the general formula:

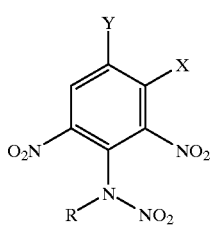

(II)

in which R, X and Y have the meanings given above, and these have to be removed from the final product in order to obtain the desired dinitroaniline in purified form.

Methods for converting N-nitro derivatives of dinitroanilines into dinitroanilines are described in patent literature such as U.S. Pat. No. 4,391,992, European patent application EP-A-0 024 503 and European patent application EP-A-0 049 384, herein incorporated by reference.

The methods described therein provide for the treatment of dinitroanilines containing variable quantities of N-nitro-dinitroanilines, in the presence of specific organic solvents which are not miscible with water, such as 1,2-dichloroethane, chloroform, monochlorobenzene or carbon tetrachloride, with an aqueous solution of a base such as an alkali-metal hydroxide or carbonate or ammonium hydroxide in quantities sufficient to bring the pH to values greater than 7. In order for this treatment to be effective, according to the prior art, it is necessary to add to the two-phase aqueous-organic reaction mixture suitable additives which, by acting as phase-transfer catalysts (PTCs) enable the base dissolved in the aqueous phase to come into intimate contact with the organic phase, thus enabling the denitration reaction to be performed in accordance with the following scheme:

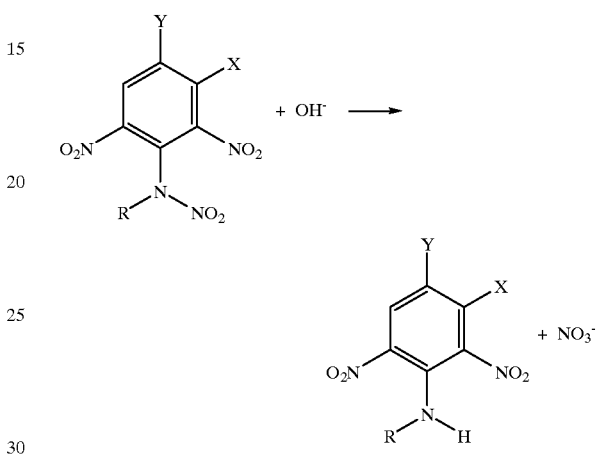

Known phase-transfer catalysts comprise phosphonium salts, symmetric or asymmetric ammonium salts, crown ethers, pyrazolium salts, alkylpyridinium salts, mixtures of anionic and non-ionic emulsifiers, -onium salts, polyethylene glycols and mono- and di-esters of orthophosphonic acid with ethylene oxide adducts; these catalysts are typically added to the reaction mixture in proportions of from 0.15 to 4 moles per mole of N,2,6-trinitroaniline.

EP-A-0 893 431 (herein incorporated by reference) also describes a N-denitration method which operates on a two-phase aqueous-organic reaction mixture constituted by the aqueous phase of the base added and by the organic phase of the dinitroaniline of interest but in the absence of solvent. In this case also, it is necessary to use a phase-transfer catalyst.

The object of the present invention is to provide a simpler and more economical method of carrying out the N-denitration reaction.

Another object of the invention is to provide a novel method which achieves results which are wholly comparable, in terms of N-denitration, with those achieved by methods of the prior art.

The subject of the invention is a method of purifying dinitroanilines of the general formula (I) given above by N-denitration of the impurities of N,2,6-trinitroaniline contained therein, in the presence of a base selected from alkali-metal hydroxides, alkali-metal carbonates and ammonium hydroxide, at neutral or basic pH, characterized in that it comprises the treatment, with stirring, of the quantity of dinitroaniline to be purified with an alcoholic organic solvent in a quantity and at a temperature which are adequate to dissolve the mass of dinitroaniline to be purified.

The method according to the invention is effective in converting N-nitro derivatives of dinitroanilines into dinitroanilines and achieves the desired purification even in the absence of phase-transfer catalysts and emulsifiers; the absence of catalytically effective quantities of these agents thus constitutes an advantage and a preferred characteristic of the invention. The alcohols used as solvents are preferably monofunctional alcohols, preferably aliphatic alcohols having from 1 to 6 carbon atoms, such as methanol, ethanol and isopropanol; it is, however, possible to use any alcoholic solvent capable of dissolving both the dinitro- and trinitro-derivatives and an appreciable quantity of the base used, or in any case a quantity sufficient to bring the pH to the desired neutral or basic value.

With the use of an alcoholic solvent in which the base used is only slightly soluble, undissolved bottom solids may be present in the initial phase of the N-denitration reaction; to avoid the presence of the bottom solids, it is possible to add the base to the reaction medium in successive portions whilst the reaction is in progress. The quantity by weight of alcoholic solvent used is typically equal to two or three times the weight of the organic mass to be treated.

Of the various alcohols which may be used, from the point of view of the economy of the method as a whole, the use of n-pentan-3-ol, which is a byproduct without commercial uses resulting from the process for the synthesis of the aniline which is subsequently subjected to dinitration, is particularly advantageous.

The N-denitration reaction according to the invention may be performed within the dinitroaniline purification process described in EP-A-0 893 431, in the name of the Applicant, which comprises, as a first step, a denitrosation reaction performed on the dinitration product containing the dinitroaniline of interest and corresponding undesired impurities of N-nitroso- and N-nitro-dinitroaniline, in the absence of solvent and, as a second step, the denitration reaction, performed in sequence with the denitrosation reaction in the same reactor; the N-denitration reaction may be carried out in the conditions described by the present invention.

Alternatively, the N-denitration reaction according to the invention may be performed directly on the dinitration reaction product from which any solvent used in the dinitration reaction has previously been removed.

However, small residual quantities of the solvents typically used in the dinitration reaction, such as dichloroethane, are not harmful to the N-denitration reaction according to the invention, provided that it is possible, by the addition of the alcoholic solvent, to produce a substantially homogeneous solution.

The base, which is preferably constituted by sodium or potassium hydroxide, is preferably added to the alcoholic solvent used, to which the mass of dinitroaniline to be treated is added.

In the method according to the invention, the reaction medium is preferably substantially anhydrous; however, quantities of water no greater than 0.5% by weight, preferably no greater than 0.2% by weight are acceptable.

The N-denitration reaction according to the invention is preferably carried out with intensive stirring at a temperature of from about 60° C. to about 85° C., preferably at a temperature close to the boiling point of the solvent, at atmospheric pressure, for times generally of between 2 and 4 hours, until the reaction is substantially completed.

Upon completion of the reaction, the mixture thus obtained is transferred into a separator in which it is cooled to ambient temperature and in which the excess basicity is removed by successive washings with water. If excessively water-soluble alcohols such as methanol or ethanol are used, it may be necessary to add a solvent which is not miscible with water to facilitate the separation. Upon completion, it is necessary to evaporate the solvent, for example, by means of a rotary evaporator.

EXAMPLE 1 (COMPARISON)

58 g of N-(1-ethylpropyl)-2,6-dinitro-3,4-xylidine (Pendimetalin) containing 4400 ppm of N-nitro-N-(1-ethylpropyl)-2,6-dinitro-3,4-xylidine was melted in a glass reactor and 60 g of 10% aqueous NaOH was added. The two-phase mixture was stirred vigorously for 4 hours at a temperature of 85° C. Upon completion, the organic phase was separated from the aqueous phase, washed twice with 80 g of water and analyzed. The content of N-nitro-N-(1-ethylpropyl)-2,6-dinitro-3,4-xylidine remained almost unchanged.

EXAMPLE 2

15 g of N-(1-ethylpropyl)-2,6-dinitro-3,4-xylidine containing 4700 ppm of N-nitro-(1-ethylpropyl)-2,6-dinitro-3,4-xylidine, was dissolved in 50 g of n-pentan-3-ol containing 0.7% w/w of NaOH; the mixture was substantially homogeneous but had a small quantity of bottom solids constituted by the undissolved base. The mixture was brought to a temperature of 85° C. and kept at that temperature for 4 hours, after which it was washed twice with 65 g of water at a temperature of 70° C. and analyzed. The content of the above-mentioned impurity had fallen to 137 ppm.

EXAMPLE 3

59 g of N-(1-ethylpropyl)-2,6-dinitro-3,4-xylidine containing 4400 ppm of N-nitro-N-(1-ethylpropyl)-2,6-dinitro-3,4-xylidine, was dissolved with stirring in 104 g of methanol containing 1.3% w/w of NaOH, to give a homogeneous, single-phase mixture without bottom solids. The solution was left at a temperature of 65° C. for 2 hours, with continuous stirring, after which it was concentrated to recover the solvent and then washed in hot water, stirred for about 5 minutes, separated from the aqueous phase and analyzed. The content of N-nitro-N-(1-ethylpropyl)-2,6-dinitro-3,4-xylidine had fallen to a value of less than 10 ppm.

EXAMPLE 4

98 g of N-(1-ethylpropyl)-2,6-dinitro-3,4-xylidine containing 1.3% w/w of N,2,6-trinitro-3,4-xylidine was dissolved in about 300 g of isopropanol containing 0.27% by weight of NaOH. The mixture thus obtained was heated to about 80° C. with continuous stirring for 4 hours. Upon completion, the mixture was cooled to 65° C. and washed twice with about 100 g of water, after which the alcohol was stripped under reduced pressure. Analysis of the product thus obtained indicates that the impurity was about 63 ppm.

EXAMPLE 5

103 g of N-(1-ethylpropyl)-2,6-dinitro-3,4-xylidine containing 0.92% w/w of N,2,6-trinitro-3,4-xylidine was dissolved in 300 g of isopropanol containing 0.25% w/w of KOH. The treatment was carried out in the conditions described in Example 4 and upon completion, the impurity analyzed was less than 20 ppm.

EXAMPLE 6

101 g of N-(1-ethylpropyl)-2,6-dinitroxylidine containing 0.92% w/w of N,2,6-trinitro-3,4-xylidine was dissolved in 296 g of absolute ethanol containing 0.66 w/w of KOH. The treatment was carried out in the conditions described in Example 4 and the reduction in the impurity content over time, determined analytically, is given in the following table.

| Time (hours) | trinitro-xylidine (ppm) |
|---|---|
| 0 | 9200 |
| 2 | 95 |
| 4 | 90 |

What is claimed is:

1. A method of purifying dinitroaniline of the general formula:

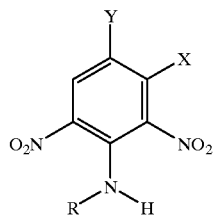

(I)

in which:
R is linear or branched $C_1$–$C_6$ alkyl, $C_4$–$C_6$ cycloalkyl, $C_1$–$C_4$ monohaloalkyl or $C_1$–$C_4$ alkoxy($C_2$–$C_4$)alkyl,
Y is $C_1$–$C_4$ alkyl, halogen or $CF_3$, and
X is hydrogen, halogen, $C_1$–$C_4$ alkyl, $C_1$–$C_4$ alkoxy, $C_1$–$C_4$ monohaloalkyl, or $C_1$–$C_4$ alkoxy($C_1$–$C_4$)alkyl, by N-denitration of the impurities of N-2,6-trinitroaniline contained therein, in the presence of a base selected from alkali-metal hydroxides, alkali-metal carbonates and ammonium hydroxide, at neutral or basic pH, the method comprising the treatment, with stirring, of the dinitroaniline to be purified with said base and with an alcoholic organic solvent, in a quantity and at a temperature which are adequate to dissolve the mass of dinitroaniline to be purified.

2. A method according to claim 1, wherein the alcoholic solvent is a monofunctional aliphatic alcohol having from 1 to 6 carbon atoms.

3. A method according to claim 1, in which the aliphatic alcohol is methanol or n-pentan-3-ol.

4. A method according to claim 1, in which the N-denitration reaction is carried out at a temperature of from 60° C. to 85° C.

5. A method according to claim 1, in which the dinitroaniline subjected to purification by N-denitration is the product resulting from the dinitration reaction of the corresponding aniline, free of any solvent used in the dinitration reaction.

6. A method according to claim 1, wherein the dinitroaniline subjected to N-denitration is not added with catalytically effective quantities of a phase-transfer catalyst or of emulsifiers.

7. A method according to claim 1, in which the dinitroaniline to be purified is Pendimetalin.

8. A method according to claim 1, in which the base is sodium or potassium hydroxide and in which the reaction medium is substantially anhydrous.

* * * * *

UNITED STATES PATENT AND TRADEMARK OFFICE
CERTIFICATE OF CORRECTION

PATENT NO.    : 5,981,795
DATED         : November 9, 1999
INVENTOR(S)   : Ravetta, Guido et al.

It is certified that error appears in the above-identified patent and that said Letters Patent is hereby corrected as shown below:

Title page,
Item [30], insert:
-- [30]  Foreign Application Priority Data
         Mar. 3, 1999    [IT]    Italy    T099A0158 --

Signed and Sealed this

Twentieth Day of August, 2002

Attest:

Attesting Officer

JAMES E. ROGAN
Director of the United States Patent and Trademark Office